(12) United States Patent
Moriuchi

(10) Patent No.: US 7,766,957 B2
(45) Date of Patent: Aug. 3, 2010

(54) BIOLOGICAL ORGAN DILATING STENT AND METHOD OF MANUFACTURING THE SAME

(75) Inventor: Yousuke Moriuchi, Tokyo (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 126 days.

(21) Appl. No.: 11/727,924

(22) Filed: Mar. 29, 2007

(65) Prior Publication Data

US 2007/0233234 A1  Oct. 4, 2007

(30) Foreign Application Priority Data

Mar. 30, 2006  (JP) .............................. 2006-095758

(51) Int. Cl.
A61F 2/06 (2006.01)

(52) U.S. Cl. .................................................. 623/1.15

(58) Field of Classification Search ................ 420/507, 420/510, 511
See application file for complete search history.

(56) References Cited

U.S. PATENT DOCUMENTS

| | | | | |
|---|---|---|---|---|
| 4,522,783 | A | * | 6/1985 | Menicucci .................. 420/503 |
| 5,833,462 | A | * | 11/1998 | Kempf et al. ............... 433/207 |
| 5,876,862 | A | * | 3/1999 | Shibuya et al. ............. 428/672 |
| 6,248,190 | B1 | * | 6/2001 | Stinson ...................... 148/519 |
| 2004/0249440 | A1 | * | 12/2004 | Bucker et al. .............. 623/1.15 |
| 2005/0121120 | A1 | * | 6/2005 | Van Dijk et al. ............ 148/678 |
| 2005/0125052 | A1 | | 6/2005 | Iwata et al. |
| 2006/0029513 | A1 | * | 2/2006 | Vincent et al. .............. 420/507 |
| 2006/0155367 | A1 | * | 7/2006 | Hines ........................ 623/1.28 |
| 2006/0200225 | A1 | * | 9/2006 | Furst et al. ................. 623/1.15 |

FOREIGN PATENT DOCUMENTS

| | | |
|---|---|---|
| DE | 299 14 242 U1 | 2/2001 |
| EP | 0 836 839 B1 | 4/1998 |
| JP | 2746755 B2 | 5/1998 |
| JP | 2003-260142 A | 9/2003 |
| JP | 2003-527931 A | 9/2003 |
| JP | 2004-505651 A | 2/2004 |
| JP | 3493195 B2 | 2/2004 |

(Continued)

OTHER PUBLICATIONS

Adnan Kastrati, et al., "Intracoronary Stenting and Angiographic Results—Strut Thickness Effect on Restenosis Outcome (ISAR-STEREO) Trial", Circulation, Jun. 12, 2001, pp. 2816-2821 (cited in paragraph [0019] of specification).

(Continued)

Primary Examiner—Corrine McDermott
Assistant Examiner—Cheryl Miller
(74) Attorney, Agent, or Firm—Buchanan Ingersoll & Rooney PC

(57) ABSTRACT

A stent is formed as a substantially tubular body possessing an outer diameter suitable for insertion into an organism, with the body being expandable when a radially outwardly directed expansion force is applied from inside the tubular body. The stent is fabricated from an alloy containing at least two noble metals selected among gold, platinum, silver, and copper, with the alloy possessing a density of not less than 14 g/cm$^3$, a proof stress of not less than 300 MPa, and a elongation-to-break of not less than 20%.

7 Claims, 2 Drawing Sheets

FOREIGN PATENT DOCUMENTS

| | | |
|---|---|---|
| WO | 93/19804 A1 | 10/1993 |
| WO | 94/16646 A1 | 8/1994 |
| WO | WO 98/31304 A1 | 7/1998 |
| WO | WO 00/13610 A1 | 3/2000 |
| WO | 00/61203 A1 | 10/2000 |
| WO | 01/72349 A1 | 10/2001 |

OTHER PUBLICATIONS

Carlo Briguori et al., "In-Stent Restenosis in Small Coronary Arteries", Journal of the American College of Cardiology, Aug. 7, 2002, vol. 40, No. 3, pp. 403-409.

European Search Report dated Jul. 4, 2007.

* cited by examiner

BIOLOGICAL ORGAN DILATING STENT AND METHOD OF MANUFACTURING THE SAME

TECHNICAL FIELD

The disclosed subject matter pertains to an organ dilating device and method of manufacturing such a device. More particularly, the disclosed subject matter relates to a biological organ dilating stent used for improvement of a stenosis portion or occluded portion generated in a lumen such as a blood vessel, a bile duct, a trachea, an esophagus, an urethra and other organs, and to a method of manufacturing such a stent.

BACKGROUND DISCUSSION

A stent is a generally tubular medical implement used to address various diseases causing stenosis or occlusion of a lumen such as a blood vessel. The stent is implanted at the stenosis portion or occluded portion of a blood vessel or other biological lumen so as to dilate the stenosis portion or occluded portion and help secure the lumen.

The stent is inserted from the outside into the inside of an organism, and implanted therein. Therefore, the stent is smaller in diameter at the time of insertion for indwelling, and is enlarged in diameter through dilation (or expansion) at the desired stenosis portion or occluded portion. By virtue of a dilation holding force of the enlarged stent, the lumen at the desired portion is dilated and held in the dilated state.

Stents are classified, by function and indwelling method, into self-expandable stents and balloon-expandable stents. A balloon-expandable stent is a stent which itself does not have a dilating function or capability. The balloon-expandable stent is inserted into a desired portion and is then dilated (plastically deformed) to be fixed in close contact with the inside surface of the desired lumen under a dilating force of a balloon located inside the stent. In using this type of stent, the above-mentioned stent dilating operation is required.

A commonly practiced procedure of implanting a coronary artery stent is as follows. To carry out a stent embedding procedure, it is necessary to introduce various catheters into a blood vessel. First, the blood vessel is secured by indwelling a sheath in a blood vessel (for example, mainly the femoral artery, the elbow artery or the radial artery) having an inside diameter permitting insertion of the catheters. In general, the sheath has a thin-walled plastic tube body, and a seal valve provided at the proximal end of the tube body so as to prevent leakage of blood and to permit the catheters to be inserted and removed in a substantially liquid-tight condition.

Then, a catheter called a guiding catheter is inserted in the sheath, and its tip is fixed to the desired coronary artery orifice (the right or left coronary artery orifice). As a result, a passage between the exterior and the coronary artery is secured or achieved.

Thereafter, a guide wire having a small diameter of about 0.014 inch is inserted, and is passed through a stenosis portion (desired portion of treatment) of the coronary artery. Then, a dilating catheter fitted with a balloon at its tip is inserted along the guide wire, the balloon is dilated at the stenosis portion to dilate the stenosis portion, and the dilating catheter is removed. The balloon dilation of the stenosis portion is thus completed. Thereafter, a contrast medium is injected through the guiding catheter, and the dilated condition of the stenosis portion is checked. If the stenosis portion is found to be sufficiently dilated and no trouble is found, the procedure is finished.

However, if the dilation is deemed to be unsatisfactory or an inner membrane is found to be abraded, a stent indwelling procedure is carried out successively. In recent years, the implantation of stents has become more frequent. A stent embedding process is conducted by a method involving a biological organ dilating implement equipped with a balloon-expandable stent that is inserted along the guide wire to the stenosis portion treated as above. The balloon is dilated to cause the stent to make close contact with and expand the inside wall of the stenosis portion. This thus causes the stent to be implanted in the stenosis portion. Then, the balloon is shrunk (contracted), and the biological organ dilating implement is removed.

This stent implantation procedure is quite widely used as a generalized procedure, and many kinds of stents have been used clinically. The stent, in general, is fabricated by hollowing a single metallic tube into one of various shapes.

The basic functions required of a stent are the delivery performance and the restenosis preventive function. The delivery performance refers to the ability of the stent to be relatively easily delivered to the desired blood vessel portion. Factors related to the delivery performance include the diameter of the stent in the state of being mounted on the balloon of the biological organ dilating implement, the degree of close contact between the balloon and the stent in the mounted state, and the flexibility of the stent part in the mounted state. When the blood vessel is sharply bent or calcified, a strut (filamentous portion) constituting a part of the stent may become caught by the blood vessel portion, thereby hindering the progress or implantation of the stent.

In addition, it is known that restenosis is generated to a certain extent at the portion where the stent is implanted. The restenosis preventive function thus refers to the ability of the stent to prevent or suppress the generation of such a restenosis. Since the possible occurrence of restenosis is checked fluoroscopically, the implanted stent is required to have good radiopacity. In addition, where the stent has high radiopacity, it is easy to confirm the indwelling conditions of the stent at the stenosis portion, for example, the indwelling position of the stent and the dilated condition of the stent.

In addition, once a stent is implanted in an organism, it is difficult to remove other than by a surgical operation and so the stent should also possess high biocompatibility.

Several proposals have been made for the blank material for stents. For example, JP-A-2003-527931 (corresponding to International Application Publication No. WO01/72349) discloses stents formed from a blank material containing cobalt, chromium and other metals and having a wall thickness of not less than 25 µm. However, the stents disclosed in this document have the drawback of being low in radiopacity.

Japanese Patent Laid-open No. 2003-260142 (corresponding to U.S. Patent Application Publication No. 2005/125052) discloses stents formed of a single material having a radiopacity higher than stainless steels, such as gold and platinum, and having a wall thickness of 50 to 100 µm. Since these stent are formed of a single metal, however, they are low in mechanical strength and possess a relatively large wall thickness.

JP-A-2004-505651 (corresponding to International Application Publication No. WO00/61203) discloses noble metal alloy stents which, among various mechanical properties, are restricted with respect to their yielding point and elongation. However, the alloys used in this patent contain large amounts of palladium, which is pointed out to have the problem of acting as an allergen, so that the alloys have a high possibility of causing allergy. The noble metal alloys used in the dental field will sometimes cause a metallic allergy. As a therapeutic method to cope with the allergy, simple removal of the relevant metal (device) may be satisfactory in the dental field. However, stents cannot be removed other than by surgery. Therefore, it is dangerous to apply the noble metal alloys used in the dental field to biological organ dilating stents.

Japanese Patent No. 2746755 (corresponding to International Application Publication No. WO94/16646) and Japanese Patent No. 3493195 (corresponding to International Application Publication No. WO93/19804) disclose clad wires which are fabricated by use of two metals or alloys for the purpose of enhancing radiopacity.

SUMMARY

As mentioned above, a stent should preferably possesses various attributes. Several that are particularly important include the delivery performance and the restenosis preventive function. The particular material (blank material) used to fabricate the stent have an affect on these attributes. For example, with respect to delivery performance, the wall thickness of the stent should preferably be relatively small. If the stent possesses a relatively small wall thickness, the outer diameter of the stent mounted on a balloon will likewise be relatively small. This helps contribute to relatively smooth passage of the stent through a lumen, even a narrow and/or bent lumen, thus leading to higher or more easy deliverability.

However, it is highly possible that a reduction in the wall thickness of a stent will lead to a reduction in the mechanical properties of the stent, a lowering of the dilation holding force of the stent, and a reduction in the stent's radiopacity.

Also, from the viewpoint of the restenosis preventive function, a smaller stent wall thickness is preferred. Comparisons have been made between stents having substantially the same structure but differing in wall thickness to determine the relative rate of restenosis (Non-patent Document 1: Circulation, 2001; 103; pp. 1816-2821). In addition, comparisons have been made between various commercially available stents classified into a group of thicker-walled stents and a group of thinner-walled stents to determine the relative rate of restenosis (Non-patent Document 2: J. Am. Coll. Cardiol., 2002; 40; P.409).

These comparisons have verified that the thinner-walled stents are significantly lower in the rate of restenosis.

According to one aspect of the disclosed subject matter, a biological organ dilating stent comprises a tubular body positionable in a biological lumen and expandable radially outwardly upon application of a radially outwardly directed expansion force from inside the tubular body, with the tubular body comprising a plurality of axially arranged annular units each comprised of at least one wavy annular element, and with axially adjacent annular units being connected to one another by link parts. The tubular body is fabricated from an alloy containing gold and at least one metal selected from among platinum, silver, and copper, with the alloy being devoid of mercury, nickel, cobalt, tin, palladium and chromium. The alloy possesses a density equal to or greater than 14 g/cm$^3$, a proof stress equal to or greater than 300 MPa, and a elongation-to-break equal to or greater than 20%

According to another aspect, a biological organ dilating stent comprises a tubular body possessing an outer diameter permitting insertion of the tubular body into a biological lumen and expandable upon application of a radially outwardly directed expansion force from inside the tubular body, with the tubular body being fabricated from an alloy containing at least two noble metals selected from among gold, platinum, silver, and copper. The alloy possesses a density not less than 14 g/cm$^3$, a proof stress not less than 300 MPa, and a elongation-to-break not less than 20%.

The biological organ dilating stent is capable of being fabricated to possess a reduced wall thickness without appreciably lowering mechanical properties of the stent, the dilation holding force, or the radiopacity of the stent.

In accordance with another aspect, a method of manufacturing a biological organ dilating stent comprises preparing a tubular body formed of an alloy containing at least two noble metals selected from among gold, platinum, silver, and copper, with the alloy possessing a density of not less than 14 g/cm$^3$, a proof stress of not less than 300 MPa, and a elongation-to-break of not less than 20%, and removing portions of the tubular body by laser beam machining to fabricate a stent, with the stent possessing an outer diameter insertable into a biological lumen and expandable upon application of a radially outwardly directed expansion force from inside the tubular body.

BRIEF DESCRIPTION OF THE DRAWING FIGURES

The foregoing and additional aspects of the disclosed stent and method will become more apparent from the following detailed description considered with reference to the accompanying drawing figures briefly described below.

DETAILED DESCRIPTION

Figure 1:
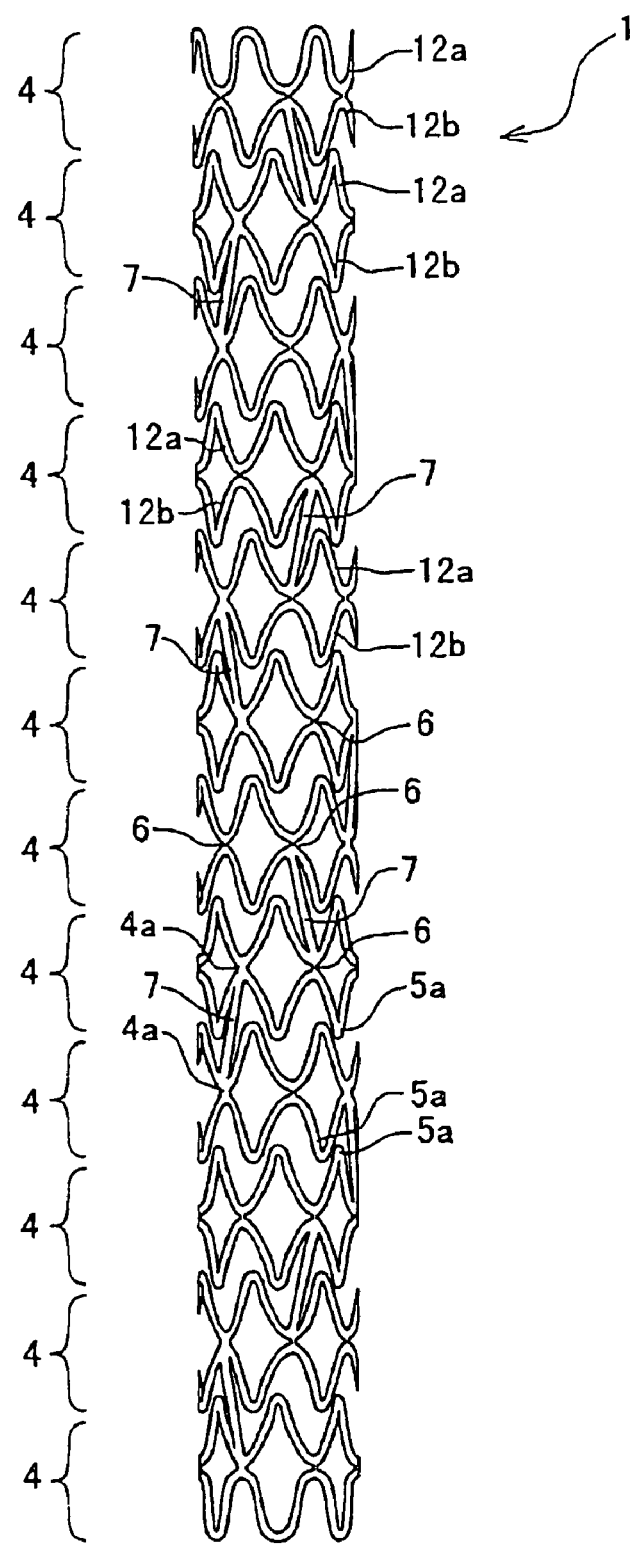
FIG. 1 is a front view of the stent according to the present invention.
Figure 2:
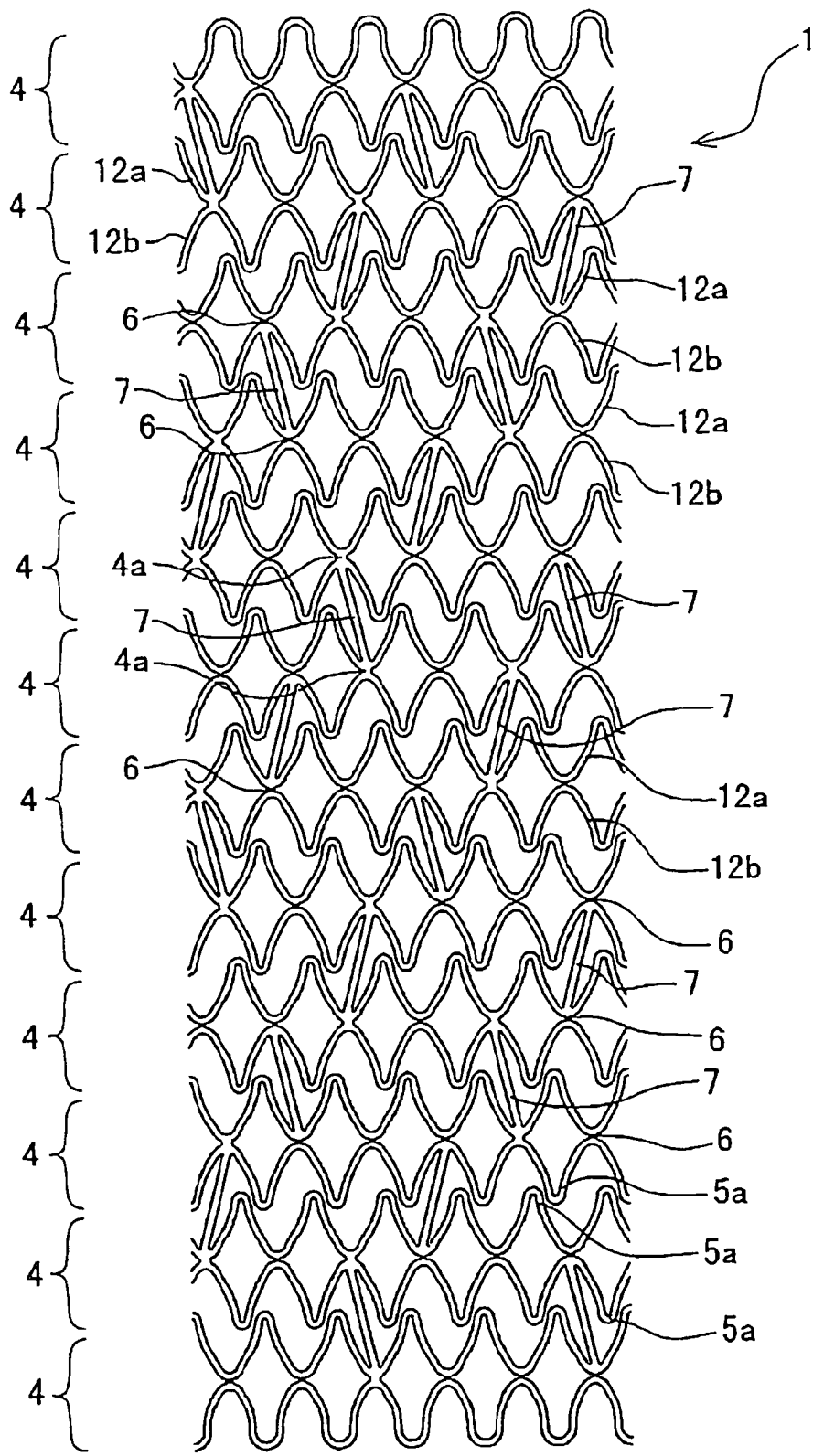
FIG. 2 is a front view of the stent illustrating the stent in a developed state in which the circumference of the stent is laid flat.

Referring to FIGS. 1 and 2, the stent disclosed here is a so-called balloon-expandable stent formed as a tubular body (inclusive of a substantially tubular body), having a diameter suitable for insertion into an organism (for example a lumen such as a blood vessel), and capable of expansion when a radially outwardly directed expansion force is applied to the stent from the inside of the tubular body.

The stent is fabricated from an alloy containing at least two noble metals selected from among gold, platinum, silver, and copper, the alloy having a density of not less than 14 g/cm$^3$, a proof stress of not less than 300 MPa, and a elongation-to-break of not less than 20%.

The shape of the stent is not particularly limited and may take any desired shape. One example of a balloon-expandable stent is shown in FIGS. 1 and 2. The stent shown in FIGS. 1 and 2 is merely intended to provide an illustration of one example. The stent is not limited in this respect as it may have different forms.

The stent 1 in this embodiment is comprised of a plurality of axially arranged annular units 4 each comprised of: a first wavy annular body 12a formed in an annular form from a wavy element having a multiplicity of bent portions 5a that include crest (ridge) portions and trough (valley) portions; a second wavy annular body 12b formed in an annular form from a wavy element having a multiplicity of bent portions 5a that include crest (ridge) portions and trough (valley) portions, with the second wavy annular body 12b disposed, in the axial and circumferential directions of the stent 1, relative to the first wavy annular body 12b so that the crest (ridge) portions are located in proximity to the valley (trough) portions of the first wavy annular body 12; and a plurality of connecting parts 6 connecting the trough portions of the first wavy annular body 12a and the crest portions of the second wavy annular body 12b. A plurality of the annular units 4 are arrayed in the axial direction of the stent 1, and link parts 7 link the axially adjacent annular units 4 at their connecting parts 6. That is, the link parts 7 extend between one of the connecting parts 6 of one annular unit and one of the connecting parts 6 of an adjacent annular unit to connect together the adjacent annular units 4. Furthermore, axially adjacent annular units 4 are connected together by several of the link parts 7 which are located at positions spaced apart from one another, at regular angular intervals around the circumferential extent of the stent in the illustrated embodiment. In the illustrated embodiment, two link parts 7 connect axially adjacent pairs of the annular units and are located at opposite positions to one another (i.e., at diametrically opposite positions considered with reference to the circumferential extent of the stent).

Thus, the stent 1 includes the plurality of the annular units 4 arrayed substantially rectilinearly in the axial direction of the stent 1, and the link parts 7 linking the wavy elements (the wavy annular bodies 12a, 12b) of the axially adjacent annular units at portions where the connecting parts 6 are formed. From another point of view, the stent 1 is a tubular body having a configuration in which a plurality of the annular units 4 are linked by the link parts 7.

The stent is fabricated from an alloy containing at least two noble metals selected from among gold, platinum, silver, and copper, the alloy having a density of not less than 14 g/cm$^3$, a proof stress of not less than 300 MPa, and a elongation-to-break of not less than 20%.

Particularly, the alloy preferably contains gold as a principal component and contains at least one noble metal selected from among platinum, silver, and copper. Gold as the principal component means that the amount of gold in the alloy (on a wt % basis) is greater than the amount of any other material in the alloy. With gold contained as the principal component, the stent can have high radiopacity and good balloon expandability, and can be constructed to possess a reduced wall thickness. Also, with at least one noble metal selected from among platinum, silver, and copper being contained as auxiliary component(s), the stent can have a reduced wall thickness without significantly reducing the mechanical properties or dilation holding force of the stent. Where only one noble metal is selected from among platinum, silver, and copper, it is preferable to select platinum.

Preferably, the alloy forming the stent preferably contains gold as a principal component and contains at least two noble metals selected among platinum, silver, and copper. Where two noble metals are selected from among platinum, silver, and copper, a combination of platinum and silver is preferable.

More preferably, the alloy contains gold as a principal component and contains all of platinum, silver, and copper.

The content of gold in the alloy is preferably in the range of 60 to 90 wt. %, particularly 65 to 80 wt. %. Thus, the content of gold in the alloy is preferably equal to or greater than 60 wt. %.

The content of platinum in the alloy, in a case where the alloy contains neither silver nor copper, is preferably in the range of 5 to 15 wt. %, particularly 7.5 to 12.5 wt. %. Where platinum is used together with silver and/or copper, the platinum content is preferably 0.1 to 15 wt. %, particularly 0.2 to 12.5 wt. %.

The content of silver in the alloy, in a case where the alloy contains neither platinum nor copper, is preferably in the range of 0.1 to 25 wt. %, particularly 0.3 to 20 wt. %. Where silver is used together with platinum and/or copper, the silver content is preferably 0.1 to 20 wt. %, particularly 0.3 to 17 wt. %.

The content of copper in the alloy, in a case where the alloy contains neither platinum nor silver, is preferably in the range of 0.1 to 30 wt. %, particularly 0.3 to 25 wt. %. Where copper is used together with platinum and/or silver, the copper content is preferably 0.1 to 20 wt. %, particularly 0.3 to 16 wt. %.

The functional attributes and conditions required of the balloon-expandable stent include those mentioned above. Further, the required functional attributes and conditions desirably include, by way of example, the stent possessing desirable expansive strength, a crossing profile, compatibility to the diameter of guiding catheter (for example, whether or not the stent can be used with a 5-Fr guiding catheter), flexibility in the mounted condition, clipping force, flexibility of the stent alone, vessel coverage, radiopacity, MRI compatibility and good surface condition.

As a result of the investigation associated with the development of the stent disclosed herein, it has been discovered that these functions and conditions can be achieved to certain extents by use of the stent forming blank material as abovementioned. In the stent disclosed herein, the use of the above-mentioned blank material provides a stent having particularly excellent biocompatibility, radiopacity, and MRI compatibility, while at the same time capable of being produced with a reduced stent wall thickness.

The outer diameter of the stent in the non-expanded state is preferably about 0.6 to 1.8 mm, more preferably 0.8 to 1.6 mm. The length of the stent is preferably about 8 to 40 mm, more preferably 10 to 30 mm. The wall thickness of the stent is preferably about 30 to 100 μm, more preferably 40 to 60 μm. The outer diameter of the stent upon being formed (before compression) is preferably about 1.5 to 3.5 mm, particularly 2.0 to 3.0 mm.

The stent disclosed here preferably has a wall thickness of not more than 50 μm. With the wall thickness of the stent dimensioned in this way, it is advantageously possible to achieve a reduction in the rate of restenosis.

In a relatively large diameter blood vessel, for example a blood vessel with an outside diameter of 3.5 to 4.5 mm, the rate of restenosis is relatively low. However, when a stent with a wall thickness of 0.15 mm is implanted in a relatively small blood vessel of 3.5 mm or less outer diameter, for example a 2.5 mm outer diameter blood vessel, the blood vessel lumen size is 2.2 mm and the proportion of the wall thickness based on the blood vessel outer diameter is 12%. In the case of a stent with a wall thickness of 0.05 mm, the diameter of the lumen is 2.4 mm, and the proportion of the wall thickness based on the blood vessel diameter is only 4%. Thus, the degree of relative influence of the wall thickness is higher as the blood vessel diameter is smaller. As the wall thickness is further increased, turbulence of the bloodstream could be generated to cause thrombus more easily, and the influence of blood platelets could increase, raising the rate of restenosis. Further, a thin-walled stent also possesses a relatively small diameter when mounted on a balloon, thus facilitating passage through a stenosis portion. For example, when a stent of 0.15 mm in wall thickness is mounted on a balloon of 1 mm in outer diameter, the outer diameter in the mounted condition is 1.3 mm, and the proportion of the stent wall thickness is 23%. On the other hand, if the wall thickness is 0.05 mm, the outer diameter in the mounted condition is 1.1 mm, and the proportion of the stent wall thickness is only 9%. Thus, a smaller diameter imparts higher delivery performance of the stent. In addition, it permits the use of a smaller guiding catheter, which helps facilitate or improve the inserting procedure. In addition, the step between the balloon and the stent is lessened or reduced so that the stent can be delivered without being caught by a blood vessel possessing severe ruggedness due to atheroma or by a calcified blood vessel.

However, where the form of stent is fixed, a reduction in wall thickness typically decreases the radiopacity of the stent and reduces the ability of the stent to withstand radially inwardly directed forces (compressive forces). In order to maintain the ability to withstand radial forces even in a thin-walled stent, a contrivance in stent shape may be possible. In the stent disclosed here though, a blank material having physical properties suitable for a thinned-walled stent is selected to address this.

Sufficient proof stress and elongation-to-break are physical properties of the stent considered in the construction of the stent disclosed here. The proof stress is the force required to pull the blank material so as to leave a permanent strain of 0.2%. Proof stress is expressed in $N/mm^2$ or MPa units. On the other hand, the elongation-to-break is a physical property expressing the elasticity or softness of the blank material. In the case of metals, frequently, the proof stress and the elongation-to-break are opposite or inverse to each other. That is, in general, a higher proof stress is associated with a lower elongation, and a higher elongation is associated with a lower proof stress. The same applies when a blank material is subjected to hardening and annealing. Specifically, when hardening of a blank material is conducted by heating at a high temperature and then cooling rapidly, the proof stress is increased or raised, but the elongation is reduced or lessened, and so the blank material is relatively brittle. On the other hand, when a blank material is annealed by cooling over a long time, the proof stress is reduced, but the elongation is enhanced or increased. In the case of a stent, it may be thought that in order to enhance the ability of the stent to withstand a radially inwardly directed force, the elongation may be low if the proof stress is high. However, the stent should possess relatively good durability and, therefore, it should possess good elongation. Since a stent is generally implanted in an artery, it is repeatedly subjected to vibrations of the artery and, therefore, should possess good durability. Therefore, a hard and brittle blank material is typically not suitable for stents. Accordingly, a blank material for the stent is preferably high in proof strength and high in elongation-to-break.

JP-A-2004-505651 mentioned above proposes noble metal alloy stents which are restricted as to yielding point and elongation among its various mechanical properties, wherein the yielding point (proof stress) is not less than 200 $N/mm^2$ and the elongation is not less than 8%. The cobalt-chromium alloy MP35N as a commercially available blank material for stents has a elongation-to-break of not less than 17%. In view of this, it is considered that the alloy used to form the stent disclosed here should have a elongation-to-break of not less than 20% (the elongation-to-break is preferably equal to or greater than 20%). In addition, the alloy should have a proof stress of not less than 300 MPa (the proof stress is preferably equal to or greater than 300 MPa), taking into account the rated value of proof stress of stainless steel SUS316L of not less than 190 MPa multiplied by a safety factor.

A problem particularly important as to the fluoroscopic contrast property of the stent is whether or not the stent itself can be distinguished under fluoroscopic observation. In situations in which the stent cannot be confirmed under fluoroscopic observation, if it becomes necessary to cause another stent to indwell in series with the former stent, it is virtually impossible to confirm the position of the already indwelling stent and so it is impossible to accurately position the newly indwelled stent. If a gap is present between the two stents, there is a high possibility that restenosis will be generated there. In addition, in situations in which restenosis or a like symptom occurs after a period of several days to several months from the time of placement of a stent, it may be difficult to perform accurate diagnosis if the stent cannot be confirmed under fluoroscopic observation. Thus, it is important that the stent be capable of being fluoroscopically observed and confirmed. Based on an analysis of commercially available stents which can be optimally seen under fluoroscopic observation, it was found that the density of the stents is 10 $g/cm^3$ and the wall thickness was about 120 μm. In view of this, stents of 50 μm in wall thickness were fabricated in trial from various alloys differing in density, and the stents were compared with each other in radiopacity. As a result, it has been found that the density of the stent, or the material forming the stent, should be not less than 14 $g/cm^3$ (the density is preferably equal to or greater than 14 $g/cm^3$). More preferably, the density should be not less than 15 $g/cm^3$ (the density is more preferably equal to or greater than 15 $g/cm^3$).

In addition, the stent blank material is preferably high in biocompatibility. One of the problems associated with biocompatibility is metallic allergy. Even as to stainless steel SUS316L which is a blank material used most frequently at present for balloon-expandable stents, it is necessary to call attention in relation to metallic allergy. Metals for dental use frequently have allergy problems. A metal in the mouth is dissolved in saliva, and the metallic ions are circulated throughout the patient's body, and so it is unknown at what part of the body an allergic reaction may occur. To examine or determine which metals cause an allergy, the patch test is used. In this test, about 17 kinds of metal pieces are adhered to the back or the like, and allergic reactions are checked after several days. After an investigation by the patch test to determine which metals tend to cause an allergic reaction, it is found that mercury, nickel, cobalt, tin, chromium, and palladium have the tendency, in this order of decreasing frequency, to cause an allergic reaction. Advantageously, the blank materials or alloys used to manufacture the stent disclosed here are selected to not contain any of those metals. In addition, since iron as an elemental metal is susceptible to oxidation, and iron is a magnetic material as described below, the blank materials or alloys used to fabricate the stent here do not contain iron as a component. On the other hand, gold, platinum, silver, and copper are much less likely to cause an allergic reaction (i.e., the frequency with which they generate an allergy is relatively low) and so alloys containing these metals are less likely to cause an allergy and, therefore, are high in biocompatibility.

Because the blank materials or alloys used to manufacture the stent here do not contain iron, nickel, and cobalt, which are ferromagnetic materials, the alloys are free of, or very low in, magnetism. The alloys will thus not cause any significant influence on the MRI images. MRI is a diagnosing apparatus utilized particularly for diagnosing the abdomen and the head, and where the stent is implanted in the carotid artery or the intracranial artery, the stent does not influence the image, which is advantageous. Since stainless steels are sometimes-highly magnetic, they may cause halation in MRI images, or the stent may be moved under the strong magnetism of MRI. In general, therefore, MRI diagnosis is not utilized for at least several months following implantation of a stainless steel stent.

Set forth below is a description of a method of manufacturing the biological organ dilating stent described here. The disclosed method is implemented to manufacture a biological organ dilating stent formed as a substantially tubular body, having a diameter suitable for insertion into a biological lumen, and adapted to be expanded when a radially outwardly directed expansion force is applied to the stent from inside of the substantially tubular body. Generally speaking, the method involves preparing a tubular body formed of an alloy containing at least two noble metals selected from among gold, platinum, silver, and copper, with the alloy possessing a density of not less than 14 $g/cm^3$, a proof stress of not less than 300 MPa, and a elongation-to-break of not less than 20%. After formation of the tubular body, a side surface of the tubular body is partly removed by laser beam machining so as to fabricate a stent formed body. The removal of parts of the side surface of the tubular body results in a stent having a configuration such as illustrated by way of example in FIGS. 1 and 2.

More specifically, the tubular body is initially prepared using the alloy(s) mentioned above. The tubular body can be produced by a method in which the above-mentioned alloy is subjected to hot pressing, cold pressing or extrusion to form a large-diameter pipe, the pipe is repeatedly subjected to die drawing so as to reduce the pipe size to a predetermined wall thickness and a predetermined outside diameter, and, if necessary, the surface of the radially reduced pipe is polished, either chemically or physically.

Then, removal of parts (spaced apart portions) of the side surface of the tubular body formed of the above-mentioned alloy is carried out by laser beam machining to form a stent formed body.

The removal of parts or portions of the tubular body can be conducted by, for example, cutting through use of laser beam machining (e.g., YAG laser beam machining). Specifically, a laser beam machining (primary machining) step is conducted in which the side surface of the alloy tubular body is irradiated with a laser beam to remove unrequired parts of the tubular body, thereby initially machining the tubular body roughly into a desired stent shape. Subsequently, a chamfering step (secondary machining) is conducted in which edges of the stent formed body resulting from the laser beam machining treatment are ground off. By way of example, the chamfering step can be conducted by a sandblasting treatment using hard particulates. The sandblasting treatment advantageously performs deburring and chamfering.

In situations where thermally denatured portions are formed at the peripheral edges of the stent formed body upon laser beam machining, removal of the thermally denatured portions may be conducted. The removal of the thermally denatured portion can be carried out by utilizing any of various existing treatments and polishing methods. Examples include magnetic polishing, barrel polishing, sandblasting by use of glass beads or the like, electrolytic polishing, chemical polishing, and polishing by use of a rotary tool. The thermally denatured portions of the surface have, in many cases, been hardened and rendered more brittle. Therefore, attention must be paid to the thermally denatured portions, as they would tend to crack under a force and stress would be concentrated on the crack, and the crack or the like could engulf also portions which have not been thermally denatured. This generates a distinct difference in a durability test or the like. In addition, if the polished condition or smoothness of the stent surface is poor, coagulation factors such as blood platelets in blood would adhere thereto, highly probably generating a thrombus. Therefore, attention should be paid to this point.

EXAMPLES

The description below describes specific examples of the stent disclosed herein.

Examples 1 to 4

Using alloys having the compositions shown in Table 1 below, four alloy tubular bodies having an outside diameter of 2 mm and a wall thickness of 0.06 mm were produced. These tubular bodies were subjected to laser beam machining by use of YAG laser according to a known method to fabricate stents having the configuration shown in FIG. 1.

TABLE 1

|  |  | Ex. 1 | Ex. 2 | Ex. 3 | Ex. 4 |
|---|---|---|---|---|---|
| Density (g/cm$^3$) | | 15.4 | 16.6 | 15.2 | 16.7 |
| Proof stress (MPa) | | 380 | 686 | 315 | 600 |
| Elongation (%) | | 42 | 20 | 38 | 21 |
| Composition (wt. %) | Gold | 71 | 75 | 75 | 70 |
|  | Platinum | 3.9 | 7 | 0.4 | 8.5 |
|  | Silver | 12.3 | 5.5 | 9 | 13.4 |
|  | Copper | 12.3 | 5.5 | 14.6 | 7.5 |
|  | Others | 0.6 | 7 | 1 | 0.6 |

Comparative Example

Using stainless steel SUS316L, a pipe having an outside diameter of 2 mm and a wall thickness of 0.1 mm was produced. This pipe was then used to produce a stent having the same shape as in Examples 1-4.

The stents obtained in Examples 1-4 and the stent obtained in the Comparative Example were evaluated as follows.

(1) Evaluation of Radial Force Withstanding Ability

Each of the stents was mounted onto a blood vessel dilating balloon of 20 mm in length and 3.0 mm in diameter, and the balloon was dilated at a prescribed pressure to obtain a stent having an inside diameter of 3.0 mm. The stent was laid on its side and was pressed in the vertical direction (a radial force was applied), and the force under which the displacement amount reached 2 mm was measured. The measured force for each of the stents in Examples 1-4 was compared to the measured force for the stent of Comparative Example to determine the relative force applied to achieve the noted displacement. The results are shown in Table 2. By way of example, the force under which the displacement amount for Example 2 reached 2 mm was measured and compared with the force under which the displacement amount for the Comparative Example reached 2 mm, and the results in Table 2 show that a higher force was required for Example 2.

(2) Evaluation of Radiopacity

Each of the stents of 3 mm in inside diameter was shot by a radiographic apparatus, and radiopacity thereof was evaluated. The sample was placed on a 15 mm-thick aluminum plate likened to a bone, and was shot under the condition of about 73 KV/500 mA. Since the difference between the images of the stent and the aluminum plate was distinct, the radiopacity could be visually confirmed. The results are shown in Table 2.

(3) Evaluation of MRI Artifact

An MRI contrast medium Gd-DTPA (gadolinium-diethylenetriamine pentaacetic acid) solution diluted 1000-fold in volume was placed in a plastic vessel. Each of the stents of 3 mm in inside diameter was placed in the MRI contrast medium. The assembly was shot by use of an MRI apparatus: MAGNETOM Vision 1.5T (a product by Siemens). Here, again, the difference between the stent and the MRI contrast medium was distinct, and the evaluation was conducted by visual observation. The results are shown in Table 2.

TABLE 2

|  | Ex. 1 | Ex. 2 | Ex. 3 | Ex. 4 | Comp. Ex. |
|---|---|---|---|---|---|
| Radial Force Test | comparable | higher | comparable | higher | standard |
| Opacity | good | excellent | good | excellent | bad |
| MRI | good | good | good | good | bad |
| Allergy | good | good | good | good | Ni, etc. contained |

With respect to the ability to withstand a radial force, the stents of Examples 2 and 4 which are high in proof stress showed greater abilities to withstand radial forces than that of SUS316L, which is a blank material used clinically and whose radial force withstanding ability is taken as a standard here. Even the ability of the stents of Examples 1 and 3 to withstand radial forces, though lower than those of the stents of Examples 2 and 4, were comparable to the standard. As for radiopacity, the stents of Examples 2 and 3 which are high in density showed high radiopacity, the stents of Examples 1 and 2 showed the next level of radiopacity, and the stent of Comparative Example showed little visibility or much less radiopacity. With respect to MRI artifact, the stents of Examples 1 to 4 were free of artifact and had no problem, whereas the stent of the Comparative Example showed strong artifact, which presents a problem.

Regarding allergies, the stent of the Comparative Example presented an allergy problem due to the presence of nickel, etc. It has been pointed out that nickel and molybdenum contained in the stainless steel of the coronary artery stent of Comparative Example serve as allergens, thereby possibly influencing restenosis.

From the evaluation results discussed above, the stents obtained in Examples 1 to 4 possess relatively high radiopacity, are generally free of influences of MRI, possess relatively high ability to withstand radially applied forces, and have little possibility of allergy, even when the stent wall thickness is reduced. In addition, it is expected that the rate of restenosis can be suppressed to a relatively low level by reducing the stent wall thickness.

The principles, preferred embodiments and other aspects of the disclosed stent have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A biological organ dilating stent comprising:
    a tubular body possessing an outer diameter permitting insertion of the tubular body into a biological lumen and expandable upon application of a radially outwardly directed expansion force from inside the tubular body;
    the tubular body having an outer surface adapted to contact a wall of the biological lumen and being entirely fabricated from an alloy containing 65-80% weight gold, 0.2-12.5% weight platinum, 0.3-17% weight silver, and 0.3-16% weight copper;
    the alloy does not contain any of mercury, nickel, cobalt, tin, palladium and chromium;
    the alloy possessing a density not less than 14 $g/cm^3$;
    the alloy possessing a proof stress not less than 300 MPa; and
    the alloy possessing an elongation-to-break not less than 20%.

2. The biological organ dilating stent as set forth in claim 1, wherein the tubular body possesses a wall thickness of not more than 60 μm.

3. The biological organ dilating stent as set forth in claim 1, wherein the stent has a wall thickness of not more than 60 μm.

4. A biological organ dilating stent comprising:
    a tubular body positionable in a biological lumen and expandable radially outwardly upon application of a radially outwardly directed expansion force from inside the tubular body;
    the tubular body comprising a plurality of axially arranged annular units each comprised of at least one wavy annular element, with axially adjacent annular units being connected to one another by link parts;
    the tubular body having an outer surface adapted to contact a wall of the biological lumen and being entirely fabricated from an alloy containing 65-80% weight gold, 0.2-12.5% weight platinum, 0.3-17% weight silver, and 0.3-16% weight copper;
    the alloy being devoid of mercury, nickel, cobalt, tin, palladium and chromium;
    the alloy possessing a density equal to or greater than 14 $g/cm^3$;
    the alloy possessing a proof stress equal to or greater than 300 MPa; and
    the alloy possessing an elongation-to-break equal to or greater than 20%.

5. The biological organ dilating stent as set forth in claim 4, wherein the tubular body possesses a wall thickness of not more than 60 μm.

6. A method of manufacturing a biological organ dilating stent comprising:
    preparing a tubular body formed of an alloy containing 65-80% weight gold, 0.2-12.5% weight platinum, 0.3-17% weight silver, and 0.3-16% weight copper, but not containing any of mercury, nickel, cobalt, tin, palladium, and chromium, with the alloy possessing a density of not less than 14 $g/cm^3$, a proof stress of not less than 300 MPa, and an elongation-to-break of not less than 20%; and
    removing portions of the tubular body by laser beam machining to fabricate a stent, with the stent possessing an outer diameter insertable into a biological lumen and expandable upon application of a radially outwardly directed expansion force from inside the tubular body.

7. The method of manufacturing a biological organ dilating stent as set forth in claim 6, wherein the preparation of the tubular body comprises preparing a tubular body possessing a wall thickness of not more than 60 μm.

* * * * *